US009671327B2

(12) United States Patent
Pinchuk

(10) Patent No.: US 9,671,327 B2
(45) Date of Patent: Jun. 6, 2017

(54) ULTRASENSITIVE BIOCHEMICAL SENSING DEVICE AND METHOD OF SENSING ANALYTES

(75) Inventor: Anatoliy Pinchuk, Colorado Springs, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 996 days.

(21) Appl. No.: 13/422,718

(22) Filed: Mar. 16, 2012

(65) Prior Publication Data

US 2012/0238471 A1    Sep. 20, 2012

Related U.S. Application Data

(60) Provisional application No. 61/454,288, filed on Mar. 18, 2011.

(51) Int. Cl.
| | |
|---|---|
| *G01N 21/21* | (2006.01) |
| *G01N 33/543* | (2006.01) |
| *B82Y 15/00* | (2011.01) |
| *C40B 40/00* | (2006.01) |
| *G01N 21/552* | (2014.01) |

(52) U.S. Cl.
CPC ........... *G01N 21/21* (2013.01); *G01N 21/554* (2013.01); *G01N 33/54373* (2013.01); *B82Y 15/00* (2013.01); *C40B 40/00* (2013.01)

(58) Field of Classification Search
USPC ........................................................ 506/13
See application file for complete search history.

(56) References Cited

U.S. PATENT DOCUMENTS 7,233,396 B1 * 6/2007 Hall et al. ..................... 356/369
8,314,935 B2 * 11/2012 Handa et al. ................. 356/445

OTHER PUBLICATIONS

Pinchuk et al., "Nanoparticle optical properties: Far- and near-field electrodynamic coupling in a chain of silver spherical nanoparticles," Mater. Sci. Eng. B 2008, 149:251-258.*
Haes et al., "A Localized Surface Plasmon Resonance Biosensor: First Steps toward an Assay for Alzheimer's Disease," Nano Lett. 2004, 4:1029-1034.*

(Continued)

*Primary Examiner* — Kaijiang Zhang
(74) *Attorney, Agent, or Firm* — Lathrop & Gage LLP

(57) ABSTRACT

Systems and methods biochemically sense a concentration of a ligand using a sensor having a substrate having a metallic nanoparticle array formed onto a surface of the substrate. A light source is incident on the surface. A matrix is deposited over the nanoparticle array and contains a protein adapted to binding the ligand. A detector detects s-polarized and p-polarized light from the reflective surface. Spacing of nanoparticles in the array and wavelength of light are selected such that plasmon resonance occurs with an isotropic point such that −s and −p polarizations of the incident light result in substantially identical surface Plasmon resonance, wherein binding of the ligand to the protein shifts the resonance such that differences between the −S and −P polarizations give in a signal indicative of presence of the ligand.

14 Claims, 5 Drawing Sheets

(56) References Cited

OTHER PUBLICATIONS

Endo et al., "Multiple Label-Free Detection of Antigen-Antibody Reaction Using Localized Surface Plasmon Resonance-Based Core-Shell Structured Nanoparticle Layer Nanochip," Anal. Chem. 2006, 78:6465-6475.*

Debackere, P. et al.; A Biosensor based on Surface Plasmon Interference, Proceedings Symposium IEEE/LEOS Benelux Chapter, 2006, Eindhoven, pp. 69-72.

Kravets, V.V. et al., Electrodynamic coupling in regular arrays of gold nanocylinders, J. Phys. D: Appl. Phys. 45 (2012) pp. 1-8.

* cited by examiner

ULTRASENSITIVE BIOCHEMICAL SENSING DEVICE AND METHOD OF SENSING ANALYTES

RELATED APPLICATIONS

The present document claims priority to U.S. Provisional Patent Application 61/454,288 filed 18 Mar. 2011, incorporated herein by reference.

GOVERNMENT INTEREST

This invention was made with government support under grant number DE-AC02-06CH11357 awarded by the U.S. Department of Energy. The government has certain rights in the invention.

FIELD

The herein described device relates to the fields of nanostructures and to the field of optical sensors.

BACKGROUND

Surface plasmon resonances involve collective oscillations of electrons at a boundary of a conductive metal film, or of an array of conductive metal particles, that are stimulated by the electromagnetic waves of incident light. For resonance to occur, the excitation light frequency must be near the frequency of the collective coherent oscillations of the free electrons or surface plasmon frequency. Since the surface plasmon electron oscillation frequency depends on dielectric constants of the metal film at the surface, and of medium adjacent to the metal film at the surface, changes in those dielectric constants may alter resonances.

P. Debackere, et al., *A Biosensor based on Surface Plasmon Interference*, Proceedings Symposium IEEE/LEOS Benelux Chapter, 2006, Eindhoven, pg. 69-72, describes biosensors where a surface plasmon resonance is excited and read with infrared light, the resonance measurably changing with changes in dielectric constant at a surface of the sensor due to presence or absence of analytes in adjacent media. Debackere, et al., does not describe use of conductive-particle arrays, or of surface plasmon resonances in such arrays.

Kravets V. V., Yeshchenko O. A., Gozhenko V. V., Ocola L. E., Smith D., Vedral J. V., and Pinchuk A. O., Electrodynamic coupling in regular arrays of gold nanocylinders, (2012) Journal of Physics D: Applied Physics 45 (2012) 045102, describes a method of creating arrays of gold nanocylinders having particle sizes between 50 and 200 nanometers and which exhibit surface plasmon resonances.

SUMMARY

Systems and methods for biochemically sensing a concentration of a ligand have a substrate and a metallic nanoparticle array formed onto the surface of the substrate. A linear polarized light source (−s or −p polarization) is incident on the substrate. A matrix is deposited over the nanoparticle array and has a protein adapted to binding the ligand. A detector detects s-polarized or p-polarized light from the reflective surface. The spacing of nanoparticles in the array and wavelength of light are selected to have an isotropic point such that −s and −p polarizations of the incident light result in substantially identical Surface Plasmon Resonance frequency and bandwidth, wherein binding of the ligand to the protein shifts the resonance such that differences between the −s and −p polarizations result in a signal indicative of presence of the ligand.

A biochemical sensing device, has a substrate with a metallic nanoparticle array formed on it. A light source shines through a polarizer onto the nanoparticle array, the polarizer alternating between a first and second polarization. A detector is provided to detect light from the array. A spacing of nanoparticles in the array and a wavelength of the light source are selected to provide an isotropic point such that the first and second polarizations of the incident light result in substantially identical surface plasmon resonance until an analyte binds with a protein in a matrix disposed on the nanoparticle array.

A method of sensing at least a first analyte includes depositing a first metallic nanoparticle array on a substrate, and coating the first nanoparticle array with a first matrix, the matrix containing a protein capable of binding to the first analyte. The first nanoparticle is illuminated array through a polarizer with a tunable laser, and light from the nanoparticle array is detected. A setting of a tunable laser such that detected light when the polarizer is set for a first polarization is equal to detected light when the polarizer is set for a second polarization is stored. The first matrix is then exposed to substances that may include the analyte; and a difference between detected light when the polarizer is set for the first polarization and detected light when the polarizer is set for the second polarization is measured.

DETAILED DESCRIPTION OF THE EMBODIMENTS

Figure 1:
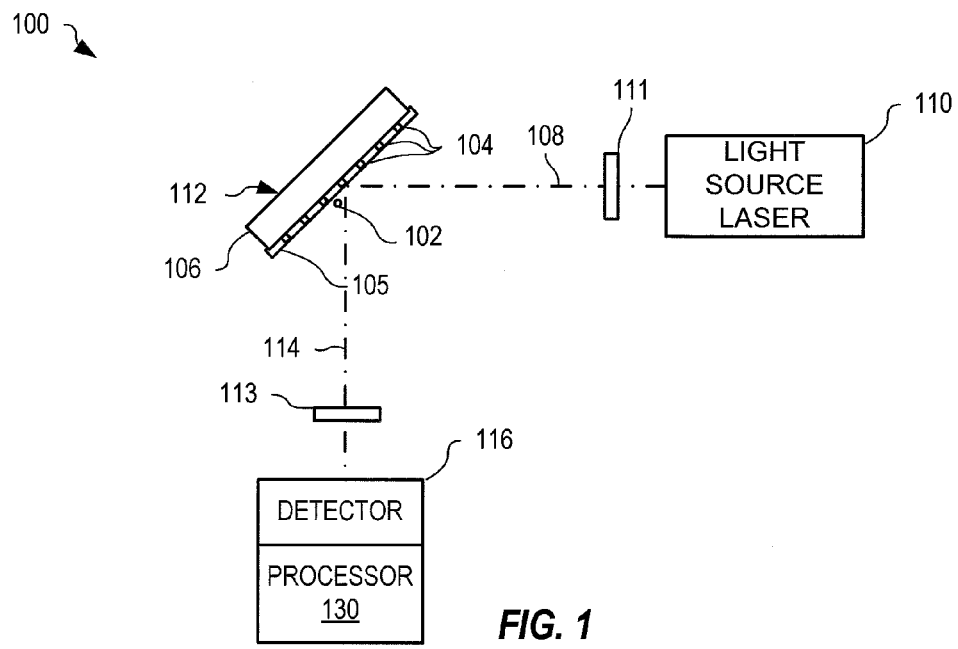
FIG. 1 shows one exemplary ultrasensitive biochemical sensing device, in an embodiment.
Figure 1A:
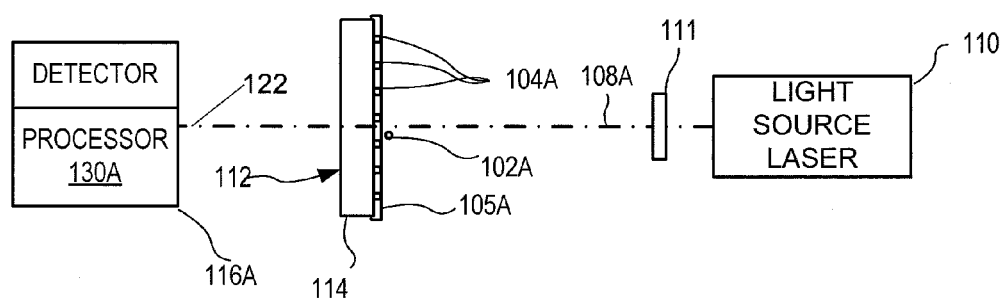

Resonant radiative electromagnetic coupling between metal plasmonic nanostructures is proposed for ultrasensitive optical biochemical sensors. Electrodynamic calculations based on multiple scattering or Generalized Mie theory show that coupled metal nanoparticles exhibit an isotropic response to a polarized electromagnetic incident field when the distance and morphology of the structures are designed to satisfy the isotropic requirements. When the distance between the particles in the array equals the wavelength of the collective Surface Plasmon Resonance (SPR), the particles in the array are resonantly coupled and become isotropic to the incident polarized light. When analyte molecules bind to the surface of metal structures, the local index of refraction changes, giving anisotropic response to the incident light. Relative shift of the SPR bands for −s and −p polarized light induced by changing the local index of refraction of the particles thus transduces chemical binding of analyte molecules into an optical signal.

Plasmonic resonances in nanoparticle arrays at convenient visible and infrared wavelengths have been observed in some metals, and not in others. Further, some metals are more corrosion resistant than others. Copper, Aluminum, Silver, Platinum, and Gold have been observed to readily exhibit these resonances, while resonances in nickel and chromium are harder to detect. While resonances have been observed in copper, and copper and aluminum are far less expensive than silver, platinum, or gold, both pure copper and some common alloys of copper oxidize easily, and aluminum's corrosion resistance is due to rapid formation of an impermeable oxide coating. Sensors having nanoparticle arrays of copper and aluminum will cease functioning when corrosion and/or oxidation sufficiently damage the nanoparticle arrays. The term "resonant metal" as used herein shall include metals, including copper, aluminum, silver, platinum, and gold, that exhibit plasmon resonances. Similarly, the term noble metal shall include resonant metals having good corrosion resistance, including silver, platinum, and gold.

The proposed nanophotonic devices employ a principle of detuning of the coupled collective resonance in resonant-metal nanoparticle arrays as a result of changing the dielectric function of the embedding host medium. The device has a higher sensitivity than usual sensors involving detuning of the Surface Plasmon Resonance (SPR) resonance in a single layer or in a single particle. There is an "isotropic" point in a system of resonantly coupled nanoparticles on a substrate, where both –s and –p polarizations of the incident light result in an identical SPR collective wavelength and bandwidth, and detuning from this isotropic point is a reference for transduction of the molecule binding into the optical signal. Changes in the dielectric constant of the embedding host matrix induce a shift of SPR wavelength of –s and –p polarizations relative to each other and this principle is used to sense the presence of the molecules, or to transduce the molecular binding event into optical signal.

While some embodiments alternate incident light between –s and –p polarizations, in alternative embodiments, in alternative embodiments light of a first and second polarization is used, where the first polarization is closer to a –s polarization than is the second polarization.

Surface Plasmon Resonance (SPR) is a collective electronic excitation in metal nanoparticles with two distinct features—strong resonant extinction of incident light at the resonant wavelength and large surface-enhanced local electric fields in close proximity to the surface of the nanoparticle. There features make noble metal nanoparticles an ideal platform for ultrasensitive, portable, low cost, multiplexed, biochemical sensors for detecting multiple analytes because a single laser system can be used to read multiple spots or wells, where each spot or well is sensitized to a different analyte.

FIG. 1 shows one sensor element of an exemplary ultrasensitive biochemical sensing device 100 for sensing the presence of a biochemical molecule 102. A noble metallic nanoparticle array 104 is formed onto a substrate 106. A beam 108 of polarized light is generated by passing light from a laser light source 110 through an adjustable polarizing element 111 and is incident upon a reflective surface 112 of substrate 106 opposite to array 104. A reflected beam 114 from surface 112 is detected by a detector 116. Also formed over the nanoparticle array is a transparent matrix 105 containing a bound biological ligand, or a protein having ligand-binding characteristics. Such proteins may include antibodies; antibodies are known to have very selective ligand-binding characteristics often capable of distinguishing between even closely-related substances.

In an embodiment, transparent matrix 105 is selected from one or more of a substance such as polylysine, aminosilane, epoxysilane sol-gel, acrylate hydrogel, carboxymethyl dextran, or nitrocellulose. In an embodiment transparent matrix 105 contains a protein, such as an antibody, having ability to bind a particular ligand of interest. Ligands of interest are typically small molecules such as, but not limited to, various drugs, water-soluble vitamins and chemical contaminants such as organophosphates, nitrogen mustards, other toxins, and sulfonamides.

In an embodiment, adjustable polarizing element 111 is capable of rapidly alternating between S and P orientations of polarized light.

Reflected beam 114 passes through an optional second adjustable polarizer 113 enroute to detector 116. In an embodiment, second adjustable polarizer 113 is set for a 45-degree angle midway between S and P polarization directions if incident light as provided by adjustable polarizing element 111. Any anisotropy between resonance in S and P polarizations will cause a difference in received light intensity between times when S polarized is applied to the sensor, and when P polarized light is applied to the sensor; this difference is amplified and measured by an associated processor 130 and provides an indication of quantity of ligands of interest. In an alternative embodiment second adjustable polarizer 113 alternates between two or more polarizations.

Constructive interference between the incident and scattered electromagnetic fields in the system of equidistantly spaced noble metal nanoparticles on a dielectric substrate results in a resonance radiative coupling between the particles providing the interparticle distance approaches to the collective SPR excitation wavelength of the system $d \approx \lambda_{SPR}$. Varying the interparticle distance around this point leads to the nonmonotonic shift of the collective SPR wavelength as a result of the constructive and destructive interference between the incident and scattered electromagnetic fields. In addition, the width of the SPR band changes non-monotonically in response to the coupling conditions (broadening or narrowing depending on the distance between the particles). Graphs 300 and 320 of FIG. 3 show theoretical scattering efficiency spectra (normalized scattering cross-section) for 50 nanometer (nm) diameter silver nanoparticles array equidistantly spaced on a glass substrate, calculated using full electrodynamic or Generalized Mie theory.

Figure 3:
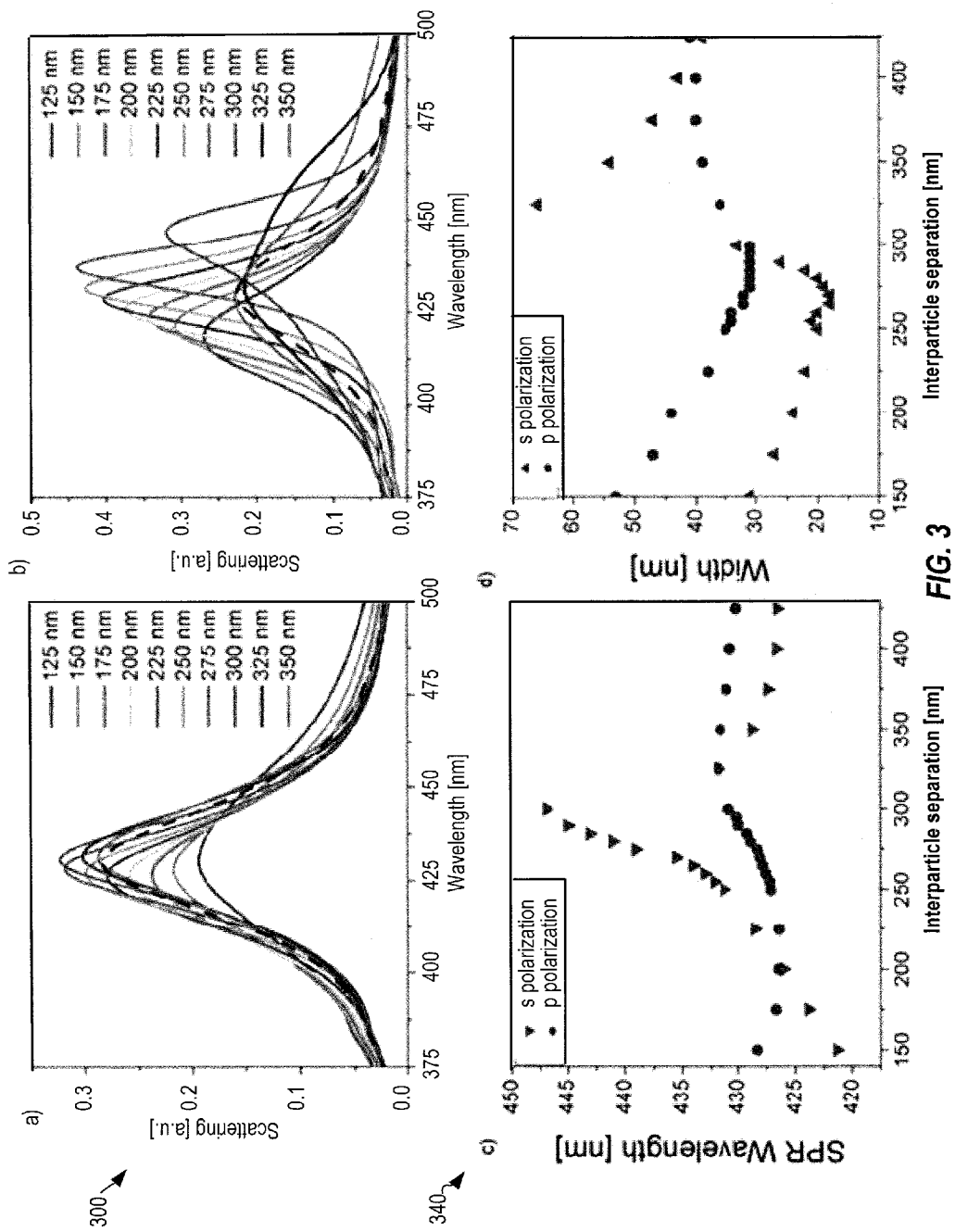
FIG. 3 shows exemplary graphs of experimental results.

When the distance between the particles in the array approaches to that of $d \approx 200$ nm and $d \approx 350$ nm for gold nanoparticles of fifty nanometer size, both s- and –p polarizations of incident light yield the same wavelength of the collective SPR excitation, see graph 340 of FIG. 3, that is, the array becomes isotropic to the incident light. Nanoparticles of different metals and/or different particle sizes may have different optimum particle spacings and wavelengths of operation. In particular embodiments, nanoparticles of between fifty to two hundred nanometers diameter are used, in arrays such the particles are spaced between eighty and four hundred nanometers apart. Small changes in the distance between the particles around these two isotropic points lead to the abrupt shift of –s and –p polarized SPR bands relative to each other, as shown in graph 340, with a stronger shift around the isotropic point $d \approx 350$ nm. We will use the relative shift of –s and –p polarized SPR bands to develop an ultrasensitive plasmonic biochemical sensor based on the resonantly coupled noble metal nanoparticles array.

In alternative embodiments, the nanoparticles of the nanoparticle arrays of the sensor have size between 50 and 200 nanometers in approximate diameter.

The collective SPR excitation of the resonantly coupled array of nanoparticles depends on both the distance between the particles and the wavelength of the incident light.

Therefore, any change in the inter-particle distance or the incident wavelength will detune the whole system from the resonance condition and lead to the anisotropic response for the −s and −p polarized incident wave. When an analyte molecule binds to the surface of a particle in the array, it changes the local index of refraction of the nanoparticle and decreases the wavelength of the incoming light. The decrease of the incident wavelength will shift abruptly the −s and −p polarized SPR bands and will lead to the anisotropic response of the sample to the incident polarized light.

The transduction of the molecular binding into an optical signal is similar to the SPR single particle spectroscopy, where the binding of a molecule to the surface of a metal nanoparticle is monitored by the shift of the localized SPR resonance. For the system of single particle SPR the wavelength of the SPR excitation depends on the local index of refraction of the particle. The major difference of the proposed device is that instead of a single nanoparticle, the collective SPR resonance of the array will be employed, and the detuning from the isotropic point of the collective SPR resonance will be used as a reference for the transduction of the molecular signal into the optical one.

The resonance condition of coupled resonance system is much more sensitive to any change of the parameters, than analogous changes in a single resonator. This provides a framework for the development of a very simple nano-optical sensor if the changes in the scattering spectra will be recognizable by a naked eye; in other embodiments an optical scanning system monitors these changes. A polarized light beam will be used for the excitation of the SPR and the change in the color or the scattering spectra for −s and −p polarized light beams will be monitored to record the molecular binding event.

FIG. 3 shows an exemplary graph 300 illustrating calculated extinction spectra of an array of equidistantly spaced 50 nm silver nanoparticles as a function of the interparticle distance and the wavelength of the p-polarized incident light. FIG. 3 also shows an exemplary graph 320 illustrating calculated extinction spectra for the same silver nanoparticles array but for s-polarization of the incident light. Graph 340 of FIG. 3 shows an exemplary shift of the SPR wavelength as a function of the distance between the particles. Graph 360 of FIG. 3 shows exemplary width of the SPR band as a function of distance between the particles.

Figure 2:
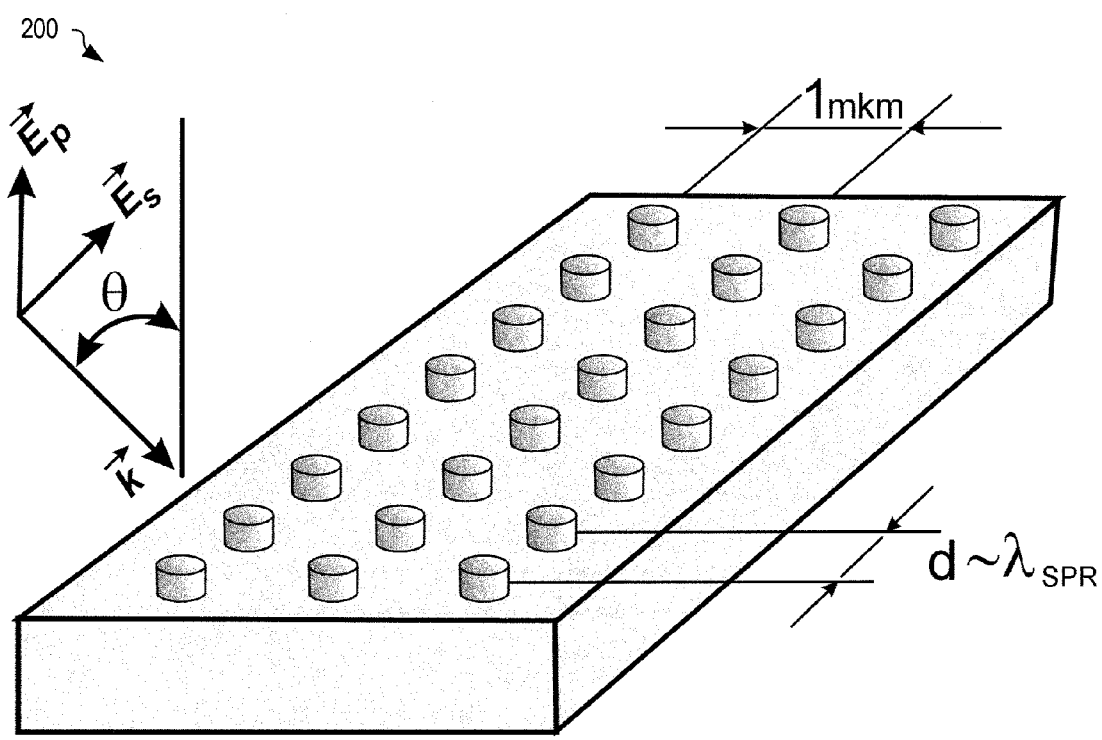
FIG. 2 is a sketch showing exemplary noble metal nanoparticle arrays on a glass substrate, in an embodiment.

FIG. 2 is a sketch showing exemplary noble metal nanoparticle arrays on a glass substrate. The distance between the particles in the array is designed to be in the regime of the resonance coupling close to the isotropic point, where both −s and −p polarization of the incident light give the same wavelength or width of the collective SPR band ($d \approx \lambda_{SPR}$=520 nm for gold nanoparticles on a glass substrate). The distance between adjacent arrays, such as arrays sensitized with matrix containing proteins adapted for binding different analytes, should be made large (e.g. on the order of 1 micrometer or larger)) to exclude the interparticle coupling between neighbor arrays.

In an embodiment 100 illustrated in FIG. 1, a sensor has an array 102 of cylindrical gold nanoparticles fabricated by a lift-off photolithographic technique, having diameter 50 nanometers and height 50 nanometers on a 10-nanometer chrome adhesion layer by an electron-beam photolithographic technique using polymethyl methacrylate resist. A center-to-center distance d between cylinders in a chain is typically within a range of 80 to 410 nanometers, the center-center distance d being chosen for optimum response at an operating wavelength of light source 110.

Figure 4:
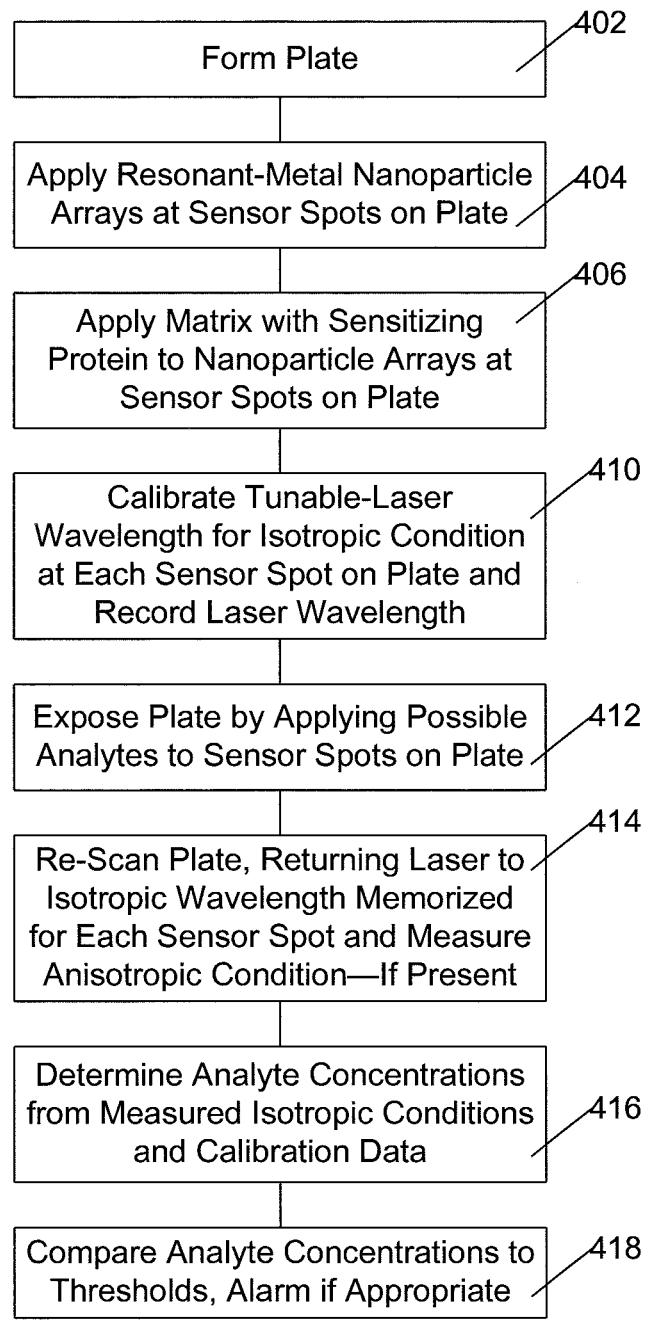
FIG. 4 is a flowchart illustrating a method of sensing for multiple analytes using the sensing device herein described.

A method of sensing for analytes based on the device described with reference to FIGS. 1, 1A, 2, and 3 is illustrated in flowchart form in FIG. 4. First, a plate is formed 402, in embodiments, the plate may have a flat analysis surface, or may have wells formed on the analysis surface. Arrays, as described above, of nanoparticles are then formed 404 from resonant metal particles at each sensor spot on the analysis surface of the plate. Each sensor spot need be only slightly larger than a beam from a sensing laser so that large numbers of sensor spots may be packed onto a plate together with any reference marks required for an optical system to locate and distinguish sensor spots.

After the nanoparticle arrays are formed, each sensor spot is sensitized by applying 406 a matrix containing a sensitizing protein. In an embodiment, the sensitizing protein is different at each of several sensor spots, such that a first sensor spot is sensitized with a protein capable of binding to a first analyte, and a second sensor spot is sensitized with a protein capable of binding to a second analyte.

The sensitized plate may be stored in a package having an oxygen-free atmosphere, such as a package having an oxygen absorber and desiccant. It is expected that plates where the nanoparticle array is formed of a noble metal may have greater shelf life than those where the array is formed of an oxidizable metal like copper, especially when some oxygen is present. The package is opened when the plate is prepared for use.

A measurement system is then calibrated 410 by scanning the plate with a beam from a sensing laser to determine a wavelength where an isotropic condition exists without analyte present. In an embodiment, the sensing laser is a tunable laser. In an embodiment an optical system scans the laser from sensor spot to sensor spot of the sensor spots on the plate, in an alternative embodiment the plate is repeatedly shifted in position such that each sensor spot is brought into a beam from the laser. The determined wavelength for each sensor spot is stored in a memory of the measurement system.

The plate is then exposed 412 to a gas or liquid that may or may not contain one or more analytes, the gas or liquid with any analytes present being applied to the sensor spots on the plate. In an embodiment, the analyte is dissolved in a solvent, the plate is washed in the solvent and the solvent is dried.

The measurement system then re-scans 414 the plate. When the laser is aimed at each sensor spot, it is returned to the wavelength at which an isotropic condition was found during the calibration 408. Response of the plate is measured at two or more polarizations, and any anisotropic condition present is measured.

In an embodiment, measurements of anisotropic conditions found during rescanning 414 of the plate are used with calibration data to determine 416 analyte concentrations. In an embodiment, these concentrations may then be reported to a user.

In a particular embodiment, determined concentrations for each analyte are compared to threshold conditions in an alarm table, and an alarm condition is generated if any analyte exceeds threshold. Alarm conditions may indicate presence of particular toxins or chemical warfare agents.

In some embodiments, such as those intended for toxins in water supplies or for detection of chemical warfare agents, the plate may be re-exposed to and re-scanned multiple times during a useable time interval before the plate is replaced.

Figure 5:
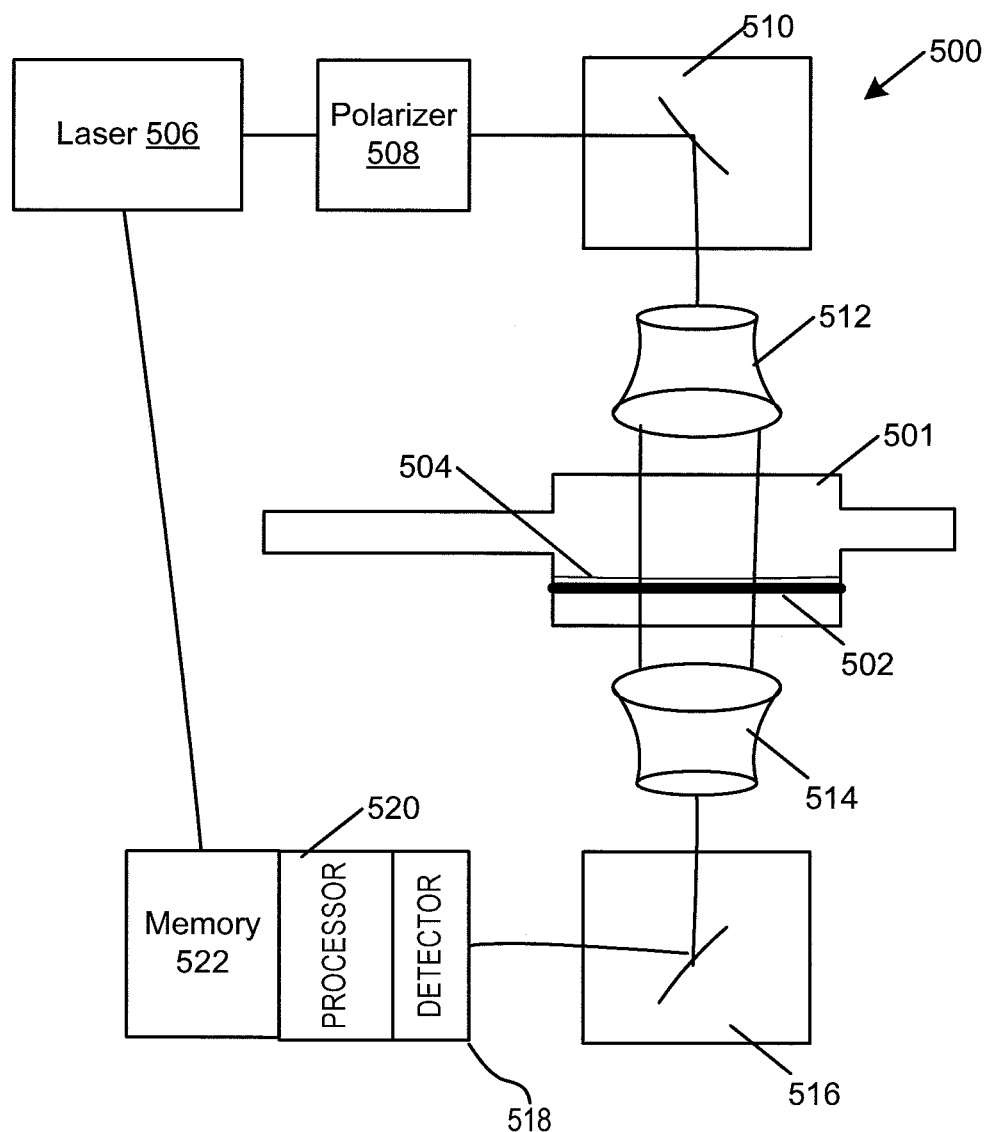
FIG. 5 is a block diagram illustrating the ultrasensitive sensing device disposed in a flow cell with a scanning system for reading the device.

In an embodiment of the system 500, for use in such applications as sensing contaminants in drinking water, where the sensor is used in a flow cell 501, as illustrated in FIG. 5, the sensor plate 502 is placed with matrix-covered nanoparticle arrays 504 exposed to fluid in the flow cell 501 and used to monitor a flowing solvent for presence of an analyte. In this embodiment, the flow cell is filled with analyte-free solvent prior to calibrating 410 the sensor array because presence of solvent may alter the index of refraction at the nanoparticle array 504.

In this embodiment, the tunable laser 506 provides a beam of light through polarizer 508 to a first scanner 510 having a telecentric lens 512 for directing light onto the sensor's matrix-covered nanoparticle arrays 504. A second telecentric lens 514 receives light from the matrix-covered nanoparticle arrays 504 through a second scanner 516 and onto detector 518. First and second scanner 516, 510, are synchronized such that the second scanner receives light from points on nanoparticle arrays 504 that are illuminated by first scanner 510. Signals from detector 518 are processed by processor 520. Memory 522 provides processor 520 with storage for laser settings of laser 506 for each sensor spot determined as isotropic during calibrating 410 the sensor array.

The nanoparticle arrays of the sensor, which may include multiple sensor spots each sensitized with protein sensitive to a different analyte, are then scanned by the scanners 510, 516, repetitively, each spot scanned with the laser tuned to the wavelength where an isotropic condition was found. Solvent that may or may not contain analyte, is then passed through the flow cell, exposing 414 the sensor spots to solvent that may contain analyte. Should analyte bind to the sensitizing proteins, an anisotropic condition will develop between –s and –p polarization at that sensor spot, and the detector 518 then measure then anisotropy and the processor 520 determines 416 analyte concentrations as heretofore described. In a particular embodiment, the analyte flowing through the flow cell is water.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An ultrasensitive biochemical sensing device, comprising:
   a substrate;
   a metallic nanoparticle array formed onto a surface of the substrate, the nanoparticles of the array having uniform size and disposed on the substrate in a regular pattern;
   a light source;
   a polarizer coupled to receive light from the light source, the polarizer configured to alternate between at least a first and a second polarization and coupled to provide light incident on the nanoparticle array; and
   a detector for detecting light from the nanoparticle array and coupled to distinguish a difference in received light intensity between times when the first polarization of light is applied to the nanoparticle array, and times when the second polarization of light is applied to the nanoparticle array;
   wherein the nanoparticle's uniform size, a spacing of nanoparticles in the array and a wavelength of the light source are selected to provide an isotropic point such that the first and second polarizations result in substantially identical surface plasmon resonance (SPR), the SPR comprising a resonant radiative coupling between nanoparticles of the array, the isotropic point altered on presence of a ligand; and
   wherein the light source is a tunable laser which is coupled to a memory in the sensing device, the memory having recorded therein a wavelength setting for the tunable laser corresponding to a wavelength where an isotropic point exists for a particular sensor spot of the metallic nanoparticle array in absence of analyte.

2. The sensing device of claim 1 wherein the metallic nanoparticle array comprises primarily of a resonant metal selected from the group consisting of copper, aluminum, silver, gold, and platinum.

3. The sensing device of claim 2, further comprising a matrix deposited over the nanoparticle array, the matrix having an embedded protein for binding the ligand, and wherein the detector provides a signal indicative of a concentration of the ligand.

4. The sensing device of claim 3 wherein the metallic nanoparticle array comprises primarily a noble metal selected from the group consisting of gold and silver.

5. The sensing device of claim 3, the nanoparticle array having a row spacing in the range of 80 to 410 nanometers.

6. The sensing device of claim 5, the nanoparticle array having a row spacing in the range of 200 to 350 nanometers.

7. The sensing device of claim 5 wherein the nanoparticle array comprises particles having diameter between fifty and two hundred nanometers.

8. The sensing device of claim 3, further comprising a second nanoparticle array, the second nanoparticle array spaced at least one micrometer from the nanoparticle array.

9. The sensing device of claim 3, wherein the matrix is a material selected from the group consisting of polylysine, aminosilane, epoxysilane sol-gel, acrylate hydrogel, carboxymethyl dextran, and nitrocellulose.

10. The sensing device of claim 3 wherein there are a plurality of sensor spots, and wherein a first sensor spot is sensitized with a first protein for binding a first ligand, and a second sensor spot is sensitized with a second protein for binding a second ligand.

11. The sensing device of claim 1 wherein the pattern is a rectangular pattern and wherein the spacing of nanoparticles in the array is a spacing of nanoparticles in rows of the pattern.

12. The sensing device of claim 11 wherein the spacing of nanoparticles in rows of the pattern is approximately a wavelength of light provided by the light source.

13. An ultrasensitive biochemical sensing device, comprising:
   a substrate;
   a metallic nanoparticle array formed onto a surface of the substrate;
   a matrix deposited over the nanoparticle array, the matrix having an embedded protein for binding the ligand;
   a light source;
   a polarizer receiving light from the light source, the polarizer alternating between at least a first and a second polarization and coupled to provide light incident on the nanoparticle array; and
   a detector for detecting light from the nanoparticle array;
   wherein a spacing of nanoparticles in the array and a wavelength of the light source are selected to provide an isotropic point such that the first and second polarizations result in substantially identical surface plasmon resonance, the isotropic point altered on presence of a ligand;

wherein the metallic nanoparticle array comprises primarily a resonant metal selected from the group consisting of copper, aluminum, silver, gold, and platinum;

wherein the detector provides a signal indicative of a concentration of the ligand; and wherein the matrix is a material selected from the group consisting of polylysine, aminosilane, epoxysilane sol-gel, acrylate hydrogel, carboxymethyl dextran, and nitrocellulose.

14. An ultrasensitive biochemical sensing device, comprising:

a substrate;

a metallic nanoparticle array formed onto a surface of the substrate;

a matrix deposited over the nanoparticle array, the matrix having an embedded protein for binding the ligand;

a light source;

a polarizer receiving light from the light source, the polarizer alternating between at least a first and a second polarization and coupled to provide light incident on the nanoparticle array; and a detector for detecting light from the nanoparticle array;

wherein a spacing of nanoparticles in the array and a wavelength of the light source are selected to provide an isotropic point such that the first and second polarizations result in substantially identical surface plasmon resonance, the isotropic point alterable by presence of a ligand;

wherein the metallic nanoparticle array comprises primarily a resonant metal selected from the group consisting of copper, aluminum, silver, gold, and platinum;

wherein the detector provides a signal indicative of a concentration of the ligand;

wherein there are a plurality of sensor spots, and wherein a first sensor spot is sensitized with a first protein for binding a first ligand, and a second sensor spot is sensitized with a second protein for binding a second ligand; and wherein the light source is a tunable laser which is coupled to a memory in the sensing device, the memory having recorded therein a wavelength setting for the tunable laser corresponding to a wavelength where an isotropic point exists for a particular sensor spot of the metallic nanoparticle array in absence of analyte.

* * * * *